US 8,202,733 B1
Jun. 19, 2012

(12) United States Patent
Javadi

(10) Patent No.: US 8,202,733 B1
(45) Date of Patent: Jun. 19, 2012

(54) SYSTEM AND METHOD FOR OBTAINING A DIFFERENTIAL FLOW RATE

(76) Inventor: Shervin Javadi, Monte Sereno, CA (US)

( * ) Notice: Subject to any disclaimer, the term of this patent is extended or adjusted under 35 U.S.C. 154(b) by 920 days.

(21) Appl. No.: 12/002,024

(22) Filed: Dec. 14, 2007

Related U.S. Application Data

(60) Provisional application No. 60/875,748, filed on Dec. 18, 2006.

(51) Int. Cl.
*G01N 15/06* (2006.01)
*G01N 33/00* (2006.01)
*G01N 33/48* (2006.01)

(52) U.S. Cl. .......... 436/180; 436/43; 436/63; 436/174; 422/50; 422/68.1; 422/81; 422/82; 422/501; 422/502; 422/503; 422/504; 422/505; 422/509

(58) Field of Classification Search .......... 436/43, 436/174, 180
See application file for complete search history.

(56) References Cited

U.S. PATENT DOCUMENTS

| | | | | |
|---|---|---|---|---|
| 5,040,890 A * | 8/1991 | North, Jr. | ............ | 356/72 |
| 5,691,633 A * | 11/1997 | Liu et al. | ............ | 324/71.1 |
| 7,242,474 B2 * | 7/2007 | Cox et al. | ............ | 356/338 |
| 7,473,529 B1 * | 1/2009 | Porter et al. | ............ | 435/6 |
| 7,553,453 B2 * | 6/2009 | Gu et al. | ............ | 422/537 |
| 7,758,811 B2 * | 7/2010 | Durack et al. | ............ | 422/73 |
| 7,760,351 B2 * | 7/2010 | Cox et al. | ............ | 356/246 |
| 2005/0105077 A1 * | 5/2005 | Padmanabhan et al. | ............ | 356/39 |
| 2005/0112541 A1 * | 5/2005 | Durack et al. | ............ | 435/2 |
| 2007/0031289 A1 * | 2/2007 | Cox et al. | ............ | 422/73 |
| 2007/0212262 A1 * | 9/2007 | Rich | ............ | 422/73 |
| 2009/0176271 A1 * | 7/2009 | Durack et al. | ............ | 435/40.5 |
| 2010/0248362 A1 * | 9/2010 | Durack et al. | ............ | 435/366 |

OTHER PUBLICATIONS

"Hydrodynamic focusing for vacuum-pumped microfluidics," Microfluid Nanofluid (2005), 1, pp. 280-283; published online: Mar. 31, 2005.*
Becton, Dickinson and company, "Introduction to Flow Cytometry: A Learning Guide", pp. 9-11, Manual Part No. 11-11032-01, Apr. 2000, US.

* cited by examiner

*Primary Examiner* — Brian J Sines
(74) *Attorney, Agent, or Firm* — Kilpatrick Townsend & Stockton LLP

(57) ABSTRACT

A system and method for obtaining hydrodynamic focusing of a first fluid. The method includes pressurizing the first fluid and a second fluid at a pre-defined pressure from a pressure source. Further, the method includes controlling the first flow rate of the first fluid by passing it through a first flow circuit. Furthermore, the method includes controlling the second flow rate of the second fluid by passing it through a second flow circuit. Moreover, the method includes passing the first and the second fluid though a converging section and hydrodynamically focusing the first fluid.

12 Claims, 8 Drawing Sheets

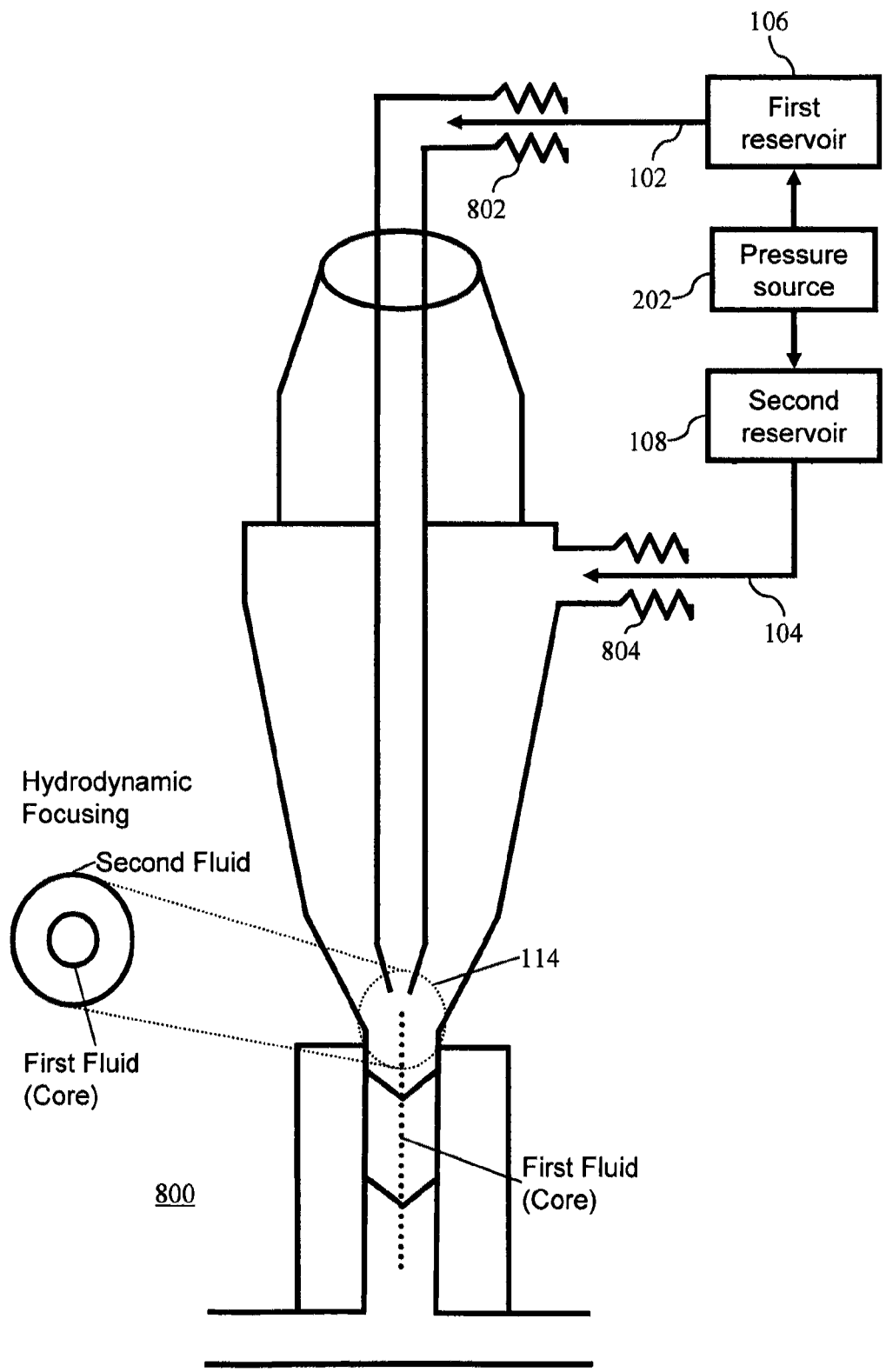

SYSTEM AND METHOD FOR OBTAINING A DIFFERENTIAL FLOW RATE

REFERENCE TO RELATED APPLICATIONS

This application claims priority of U.S. provisional application Ser. No. 60/875,748 filed Dec. 18, 2006.

FIELD OF INVENTION

The invention disclosed here relates in general to a field of fluid dynamics, and more particularly, to obtaining a differential flow rate between two fluids which is particularly suitable for fluid analysis.

BACKGROUND

In fluid dynamics, the volumetric flow rate is defined as the volume of a fluid flowing through a point per unit time. The volumetric flow rate is in direct proportion to the average flow velocity of the fluid and the cross-sectional area of the passage through which the fluid is flowing.

$$Q = Av \quad \text{(Equation 1)}$$

Where
Q Volumetric flow Rate
A Cross-sectional Area
v average flow velocity

The difference between the volumetric flow rates of two fluids is known as the differential volumetric flow rate. For example, for two fluids flowing at a volumetric flow rate of Q1 and Q2, respectively, the differential volumetric flow rate ($\Delta Q$) is:

$$\Delta Q = |Q2 - Q1| \quad \text{(Equation 2)}$$

The differential volumetric flow rate between two fluids can be used to generate a thin stream of one of the fluids surrounded by the other fluid. The thin stream generated by using the differential volumetric flow rate between the two fluids can be utilized for various purposes. For example, in a flow cytometer, a thin stream of a sample fluid such as blood can be analyzed for its cell count, chemical composition, and the types of cells or suspended particles in it. Other examples of the sample fluid include, but are not limited to, urine, saliva and other body fluids. To generate the thin stream of the sample fluid, a stream of the fluid, annularly enveloped by a sheath fluid, is made to flow through a converged section of a cuvette or a funnel. Examples of the sheath fluid include, but are not limited to, saline and water. After passing through the converged section, the diameter of the converged stream of the sample fluid is further reduced by the effect of the hydrodynamic forces generated due to the differential volumetric flow rate between the sample fluid and the sheath fluid. This technique of generating a thin stream of the sample fluid by using a differential volumetric flow rate between the sample fluid and the sheath fluid is known as hydrodynamic focusing. The intensity of hydrodynamic focusing depends on various factors such as the type of sheath fluid and sample fluid used, the required stream diameter of the sample fluid, the geometry of the converging section, the differential volumetric flow rate, and the like. Therefore, to obtain a particular stream diameter of the sample fluid by using a specific sheath fluid, a specific differential volumetric flow rate needs to be maintained between the sample fluid and the sheath fluid.

There are various methods for obtaining the differential volumetric flow rate. In one of the existing methods, the differential volumetric flow rate is maintained by controlling the respective pressures of the sample fluid and the sheath fluid flowing through a flow circuit. The existing method is based on the relationship between the volumetric flow rate of a fluid and the fluid pressure, as detailed by Equation 3 below.

$$Q \alpha \Delta P, \text{ when the flow resistance } (R) \text{ of the flow circuit is constant} \quad \text{(Equation 3)}$$

Where
Q Volumetric flow rate
$\Delta P$ Pressure differential between the inlet and the outlet of the flow circuit In this method, the sheath fluid and the sample fluid are pressurized at different pressures by their respective pressure sources. Thus, the volumetric flow rates of the sample fluid and the sheath fluid are controlled by independently controlling their respective pressures. Consequently, the differential volumetric flow rate between the sample and the sheath fluid can also be controlled.

Since the sample fluid and the sheath fluid are pressurized by two different sources, the pressure from both the pressure sources, and the pressure variations thereof, need to be synchronized to maintain a constant value of the differential volumetric flow rate. The differential volumetric flow rate is maintained at a constant value to generate a steady value of the hydrodynamic forces, which in turn maintains a constant diameter of a core stream of the sample fluid in the center. The constant diameter of the core stream is required for analysis in various systems, for example, a flow cytometer. For the purpose of maintaining a constant differential volumetric flow rate, a feedback system with two separate regulators can be provided. This feedback system can sense a change in the pressure of one of the fluids, for example, the sample fluid and correct it or synchronously regulate the pressure of the other fluid, for example, the sheath fluid. The feedback system can include mechanical links, electronic regulators, sensors, and combinations thereof. However, the use of the feedback system makes the system and method complex, error-prone and expensive. Very often, the feedback system tends to function erratically due to changes in temperature, atmospheric pressure and various other factors. Further, the feedback system can become inaccurate due to wear and tear of the mechanical parts and a drift in the electronic parts. Typically, the mechanical parts or electronic regulators operate within a tolerance zone, for example, a pressure regulator may have a positive and negative tolerance value of 0.02 pounds per square inch (psi). It is possible that at some point of time, a first pressure regulator can operate at a positive extreme of the tolerance zone and a second pressure regulator can operate at a negative extreme of the tolerance zone. For example, for maintaining a differential pressure of 0.5 psi, where the first fluid is at 5 psi and the second fluid is at 4.5 psi the first pressure regulator maintains a pressure of 5.02 psi and the second pressure regulator a value of 4.48 psi. Consequently, a differential pressure of 0.54 psi (5.02−4.48) is obtained resulting in a cumulative error in the pressure differential of 0.04 psi, (0.54−0.50) affecting the differential volumetric flow rate between the sample fluid and the sheath fluid. Thus, it becomes difficult to synchronize the pressure variation(s) between the two pressure sources, especially within the tolerance zones. As a result, it becomes difficult to maintain a focused sample fluid stream in devices such as a flow cytometer. Furthermore, the regulators used in the feedback system are expensive. Moreover, the use of two pressure sources increases the cost of the system.

In light of the foregoing, there is a need for providing a simple and cost-effective system and method for obtaining the differential volumetric flow rate and hydrodynamic focusing.

BRIEF DESCRIPTION OF THE DRAWINGS

The preferred embodiments of the invention will hereinafter be described in conjunction with the appended drawings, provided to illustrate and not to limit the invention, wherein like designations denote like elements, and in which:

FIG. 8 illustrates exemplary laboratory equipment, in accordance with an embodiment of the present invention.

DESCRIPTION OF PREFERRED EMBODIMENTS

While the preferred embodiments of the invention have been illustrated and described, it will be clear that the invention is not limited to these embodiments only. Numerous modifications, changes, variations, substitutions and equivalents will be apparent to those skilled in the art, without departing from the spirit and scope of the invention, as described in the claims.

In an embodiment, a method for hydrodynamic focusing of a first fluid in a flow cytometer is provided. The method includes pressurizing the first fluid and a second fluid at a pre-defined pressure. The first fluid and the second fluid are pressurized using a pressure source. Further, the method includes controlling a first flow rate corresponding to the first fluid. The first flow rate is controlled by passing the first fluid through a first flow circuit. The method also includes controlling a second flow rate corresponding to the second fluid. The second flow rate is controlled by passing the second fluid through a second flow circuit. Moreover, the method includes passing the first fluid and the second fluid through a converging section of the flow cytometer. The first fluid is hydrodynamically focused in the converging section.

In another embodiment, a system for hydrodynamic focusing of a first fluid in a flow cytometer is provided. The system includes a pressure source for pressurizing the first fluid and a second fluid at a first pressure. The system also includes a first flow circuit that facilitates a flow of the first fluid with a first flow rate. Further, the system includes a second flow circuit that facilitates a flow of the second fluid with a second flow rate. The second flow rate is different than the first flow rate. Furthermore, the system includes a converging section that is hydraulically connected to the first flow circuit and the second flow circuit. The first fluid and second fluid are passed through the converging section, and first fluid is hydrodynamically focused in the converging section.

In yet another embodiment, a method for obtaining a differential flow rate between a first fluid and a second fluid is provided. The method includes pressurizing the first fluid and the second fluid at a pre-defined pressure. The first fluid and the second fluid are pressurized using a pressure source. Further, the method includes passing the first fluid through a first flow circuit, which has a first set of flow restrictors. The first flow circuit imparts a first flow rate to the first fluid. The method also includes passing the second fluid through a second flow circuit, which has a second set of flow restrictors. The second flow circuit imparts a second flow rate to the second fluid. The second flow rate is different than the first flow rate.

Figure 1:
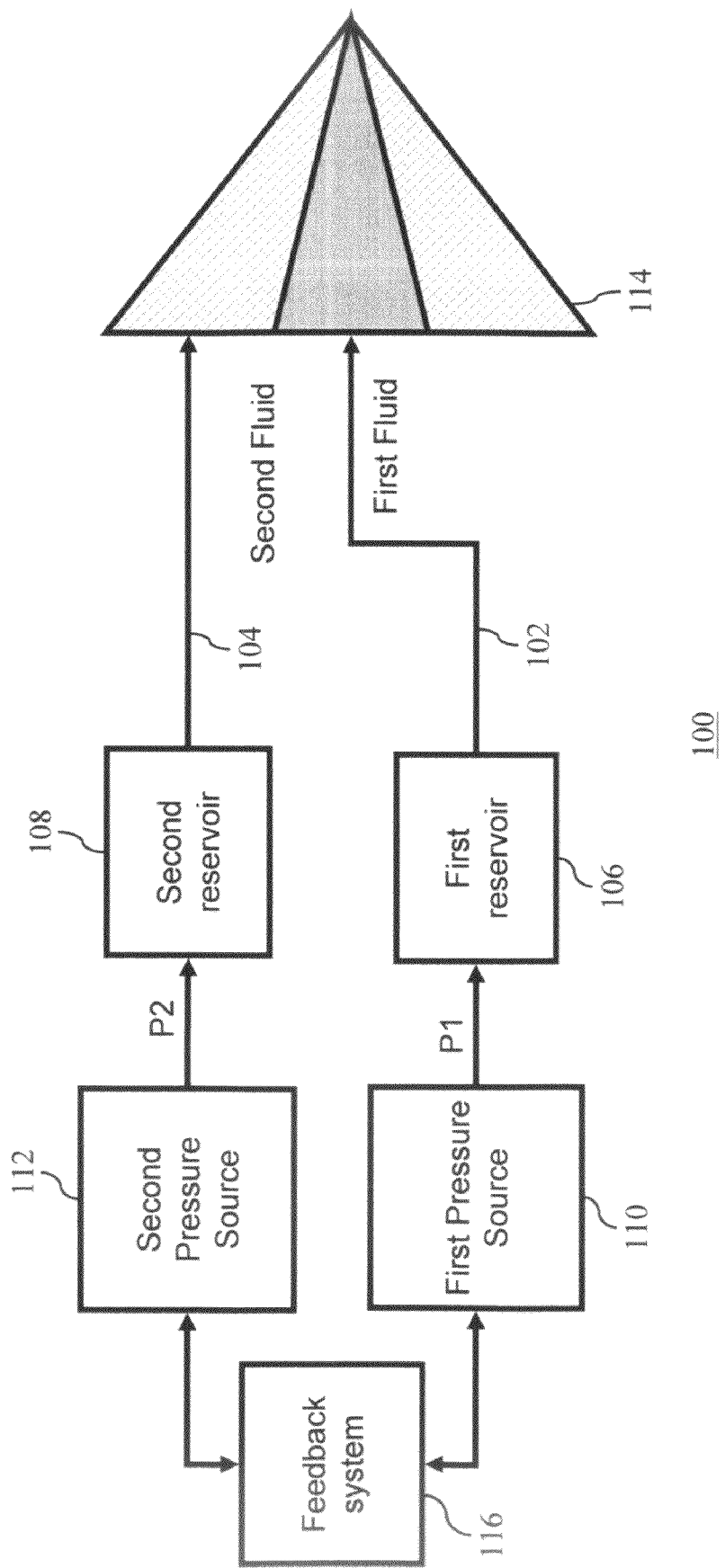
FIG. 1 illustrates a block diagram of a multi (two) pressure sources system for obtaining a differential volumetric flow rate between two fluids, as per the state of the art (prior art) before this invention.

FIG. 1 illustrates a block diagram of a multi (two) pressure sources system 100 for obtaining the differential volumetric flow rate between two fluids, as per the state of the art (prior art) before this invention. The multi pressure sources system 100 includes a first fluid 102, a second fluid 104, a first reservoir 106, a second reservoir 108, a first pressure source 110, a second pressure source 112, a converging section 114 and a feedback system 116. The multi pressure sources system 100 obtains a differential volumetric flow rate between the first fluid 102 and the second fluid 104. In an embodiment, the first fluid 102 can be a sample fluid that needs to be analyzed in laboratory equipment, for example, a cuvette in a flow cytometer. The first fluid 102 can be analyzed for counting, examining and sorting microscopic particles suspended in a stream of the first fluid 102. For some embodiments of this description, the first fluid 102 is referred to as the sample fluid. The second fluid 104 can also be a sheath fluid, which is used to generate a thin stream of the first fluid 102. The thin stream of the first fluid 102 can be generated in a cuvette of the flow cytometer. For some embodiments of this description, the second fluid 104 is referred to as the sheath fluid. The first fluid 102 and the second fluid 104 are fed from the first reservoir 106 and the second reservoir 108, respectively. In an embodiment, the first reservoir 106 can be a test tube containing the first fluid 102.

The first reservoir 106 has the first pressure source 110 connected to it. The first pressure source 110 pressurizes the first fluid 102 at the specified pressure 'P1'. Similarly, the second reservoir 108 has the second pressure source 112 connected to it. The second pressure source 112 pressurizes the second fluid 104 at a pressure 'P2', which is different from the pressure 'P1' of the first fluid 102.

The first fluid 102 and the second fluid 104 are made to flow together through the converging section 114. A constant differential volumetric flow rate ($\Delta Q$) is maintained between the first fluid 102 and the second fluid 104 by controlling their respective pressures 'P1' and 'P2' (according to Equation 3). The differential volumetric flow rate ($\Delta Q$) is maintained to obtain hydrodynamic focusing. For this purpose, the pressure 'P1' of the first fluid 102 and the pressure 'P2' of the second fluid 104 are synchronized by using the feedback system 116 between the first pressure source 110 and the second pressure source 112. The feedback system 116 senses any change in the pressure of the first pressure source 110 and may correct it or reflect the change in the second pressure source 112, or vice versa. This approximates a constant differential volumetric flow rate (ΔQ) between the first fluid 102 and the second fluid 104. However, the feedback system 116 makes the multi-pressure sources system 100 complex and not very accurate. By using a two-pressure system, the error in the differential volumetric pressure obtained can be higher than the individual tolerances of the pressure sources. This tends to decrease the stability of the differential volumetric flow rate. For instance, a pressure regulator may have a positive and negative tolerance value of 0.01 pounds per square inch (psi). In the feedback system 116, a pressure regulator for the first fluid 102 may maintain a specified pressure 'P1' with a positive tolerance of +0.01 psi ('P1'+0.01 psi) and a pressure regulator for the second fluid 104 maintain a specified pressure 'P2' with a negative tolerance of −0.01 psi ('P2'−0.01 psi). Consequently, the cumulative error increases (0.02 psi), resulting in a reduced stable differential volumetric flow rate. Further, the use of the feedback system 116 may make the multi-pressure sources system 100 erratic due to wear and tear of the mechanical parts and the drift in the electrical parts used in the feedback system 116. In addition to this, the use of two pressure sources is expensive.

Figure 2:
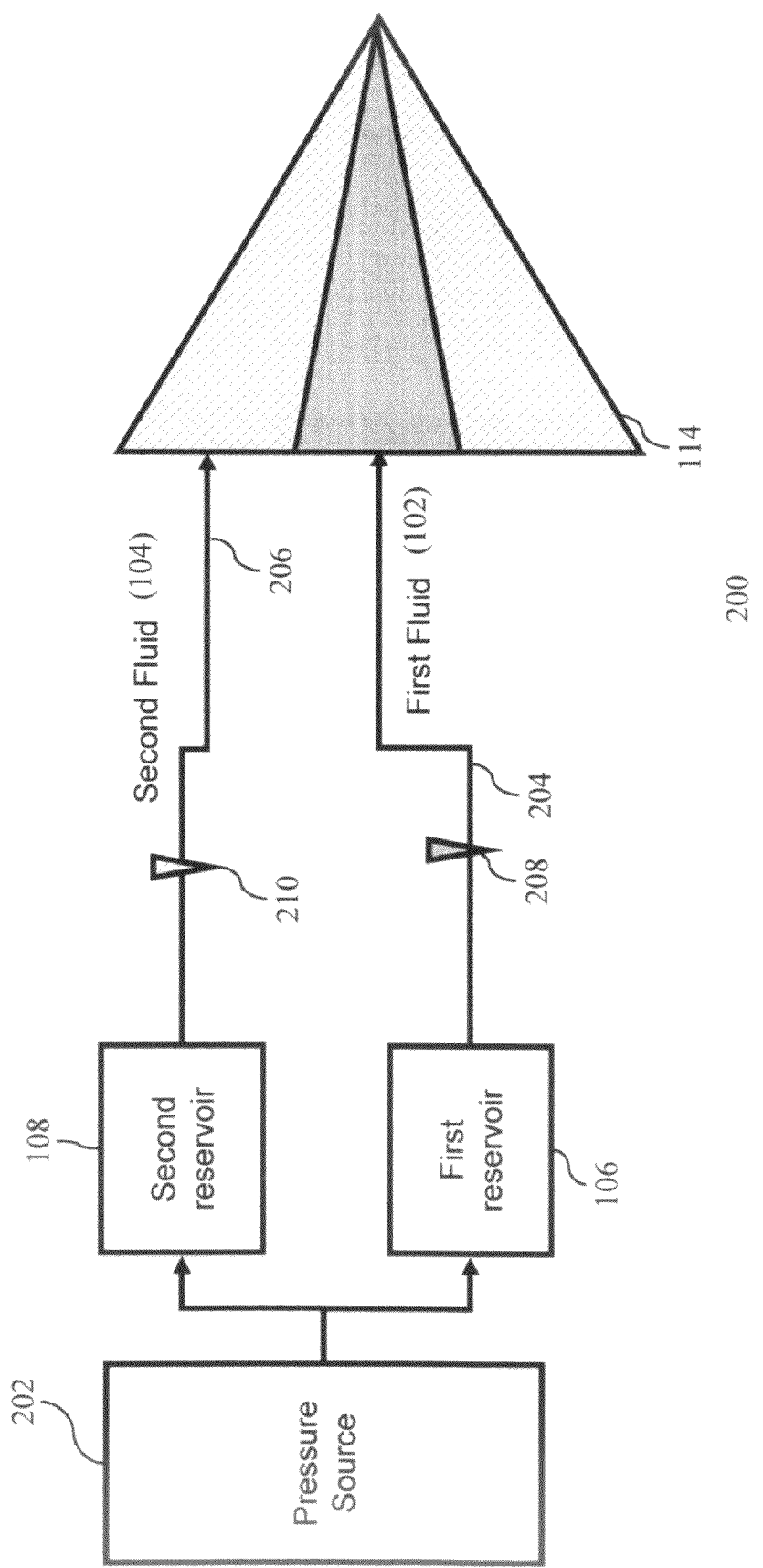
FIG. 2 illustrates a block diagram of a single pressure source system for obtaining the differential volumetric flow rate between two fluids, in accordance with an embodiment of the present invention.

FIG. 2 illustrates a block diagram of a single pressure source system 200 for obtaining the differential volumetric flow rate between two fluids, in accordance with an embodiment of the present invention. Those skilled in the art will appreciate that the single pressure source system 200 may include all or even a fewer number of components than the components shown in FIG. 2. Further, those with ordinary skill in the art will understand that the single pressure source system 200 may include additional components that are not shown here, since they are not germane to the operation of the single pressure source system 200, in accordance with the inventive arrangements.

In addition to the first reservoir 106 for the first fluid 102, the second reservoir 108 for the second fluid 104 and the converging section 114, the single pressure source system 200 is shown to include a pressure source 202, a first flow circuit 204 through which the first fluid 102 is made to flow, a second flow circuit 206 through which the second fluid 104 is made to flow, as well as a first flow restrictor 208 and a second flow restrictor 210. The pressure source 202 can pressurize one or more fluids at a specified pre-defined pressure. In other words, the pressure source 202 can pressurize one or more fluids at the same pressure. Examples of the pressure source 202 may include a positive volume-displacement device such as a syringe pump, diaphragm pump or any other pressure source, with a pressure-regulating device, such as a regulator, that can apply the same constant pressure on the first fluid 102 as well as the second fluid 104. For the purpose of describing the single pressure source system 200, the pressure source 202 can pressurize the first fluid 102 and the second fluid 104 simultaneously. The pressure source 202 is shown to pressurize the first fluid 102 at a pre-defined pressure 'P'. The pressure source 202 can also simultaneously pressurize the second fluid 104 at the pre-defined pressure 'P'. That is, the pre-defined pressure 'P' is the same pressure at which both the first fluid 102 and the second fluid 104 are pressurized. The value of the pre-defined pressure 'P' may range from 1 psi to 100 psi, for applications in flow cytometer or any other suitable pressures for the application at hand. For the purpose of description, the pre-defined pressure 'P' will be referred to as the pressure 'P' for some embodiments of the invention.

The single pressure source system 200 can obtain a differential volumetric flow rate between the first fluid 102 and the second fluid 104. The differential volumetric flow rate is required for hydrodynamic focusing of the first fluid 102, which can be analyzed for different purposes. For example, a blood sample can be analyzed for its cell count, chemical composition, types of cells, and the suspended particles in it. Examples of the first fluid 102 can include, but are not limited to, a blood sample, a tear sample, a sweat sample, a urine sample, gastric and intestinal fluids and chemical compounds. Examples of the second fluid 104 can include, but are not limited to, saline, spirit, glycerin and water.

After pressurizing the first fluid 102 and the second fluid 104 at the same pressure 'P' by using the pressure source 202, the first fluid 102 is made to flow through the first flow circuit 204, resulting in a first flow rate, or a first volumetric flow rate Q1. Similarly, the second fluid 104 is made to flow through the second flow circuit 206 at the same pressure 'P' and a second flow rate, or a second volumetric flow rate Q2. The second flow rate is different than the first flow rate. The first flow circuit 204 can include a first set of flow restrictors or flow orifices, to restrict or control the first volumetric flow rate through the first flow circuit. The first set of flow restrictors correspond to a first set of resistances. In one embodiment of the present invention, the first set of flow restrictors can be designed for a first preset value of flow resistance. Similarly, the second flow circuit can include a second set of flow restrictors. The second set of flow restrictors correspond to a second set of resistances. The second set of flow restrictors can be designed for a second preset value of flow resistance.

In another embodiment of the present invention, at least one of the first set of flow restrictors and/or at least one of the second set of flow restrictors are capable of being altered to change the flow resistance of the flow circuits. For the purpose of this description, the first flow circuit 204 is shown to include a first flow restrictor 208. Similarly, the second flow circuit 206 is shown to include a second flow restrictor 210. Examples of the flow restrictors 208 and 210 can include, but are not limited to, precision-machined holes, filters, screens, baffles, a calibrated orifice, variable cross-section tubing, constant cross-section tubing, porous restrictors, restrictor valves, needle valves and pinch valves. Furthermore, variable flow restrictors such as pinch valves may be operated manually or electronically. The single pressure source system 200 can include various combinations of these flow restrictors and flow orifices, to obtain multiple values of the differential volumetric flow rate.

The first flow restrictor 208 and the second flow restrictor 210 can have different specifications, which include the orifice diameter, the maximum permissible pressure, the maximum liquid or gas volumetric flow rate, the flow tolerance, the minimum volumetric flow rate and the operation temperature. Furthermore, these flow orifices and flow restrictors can be made from a variety of metals, metal alloys and thermoplastics.

In an embodiment, the first flow restrictor 208 and the second flow restrictor 210 are similar to each other with some differences in their specifications such as the maximum liquid or gas volumetric flow rate, the flow tolerance, the minimum volumetric flow rate values, and the like.

The types and numbers of flow restrictors in the first flow circuit 204 and the second flow circuit 206 determine the resistance of the first flow circuit 204 and the second flow circuit 206, respectively. As a result, when the flow restrictors 208 and 210 are different, the first flow circuit 204 and the second flow circuit 206 can have different resistances. The resistance of a flow circuit can be calculated by using appropriate formulae for each type of flow restrictor, for example, closed form formulae can be used for a simple round tube. Similarly, for other types of restrictors, the resistance can be determined with the aid of computational fluid dynamics or other empirical means.

Moreover, the first flow circuit 204 can maintain the first volumetric flow rate of the first fluid 102. Similarly, the second flow circuit 206 can maintain the second volumetric flow rate of the second fluid 104, which is different from the first volumetric flow rate of the first fluid 102. Referring to the equation 4, the volumetric flow rate of a fluid depends on the difference in pressure at the inlet and outlet of the flow circuit through which the fluid is flowing. Further, if the flow resistance of a flow circuit remains constant, the volumetric flow rate through the flow circuit depends on the values of the pressure at the inlet and outlet of the flow circuit. Furthermore, the outlet pressure is the pressure in the converging section 114 where the first fluid 102 and the second fluid 104 meet. Equation 4 describes the relation between the pressure difference, flow rate and flow resistance.

$$Q \propto \frac{\Delta P}{R} \quad \text{(Equation 4)}$$

Where, $\Delta P$ is the pressure difference between the inlet and outlet pressure R is a flow resistance of the flow circuit.

The terms Q and $\Delta P$ have the same meanings as described in Equation 1.

As the inlet pressure and the outlet pressure are same for both the first fluid 102 and the second fluid 104, the pressure difference $\Delta P$, is same for both the fluids. For a resistance R1 of the first flow circuit 204, the corresponding first volumetric flow rate (Q1) of the first fluid 102 is proportional to $\Delta P/R1$. Similarly, for a resistance R2 of the second flow circuit 206, the corresponding second volumetric flow rate (Q2) of the second fluid 104 is proportional to $\Delta P/R2$.

After passing through the first flow circuit 204, the first fluid 102 is made to flow through the converging section 114. Simultaneously, the second fluid 104 is also fed into the converging section 114 along with the first fluid 102, such that the second fluid 104 annularly envelops the first fluid 102. In an embodiment, the converging section can be the nozzle of the flow cytometer. In another embodiment, the converging section can be the cuvette of the flow cytometer or sections of the flow cell. In yet another embodiment, the converging section can be a combination of the cuvette and the nozzle of the flow cytometer. Other examples of the converging section 114 can include, but are not limited to, the converging portions of the laboratory equipment, a pipette, a funnel and so forth. The converging section 114 is geometrically structured to converge the flow stream diameters of the first fluid 102 and the second fluid 104 and hydrodynamically focus the first fluid 102. The first fluid 102, which is made to flow at the core of the converging section 114, shrinks in stream diameter. The first fluid 102 is focused further i.e., the stream diameter of the first fluid 102 is narrowed down further by the hydrodynamic forces between the first fluid 102 and the second fluid 104, due to the difference in the volumetric flow rates of these two fluids. Hydrodynamic focusing of the first fluid 102 occurs, irrespective of whether the first fluid 102 and the second fluid 104 are miscible or immiscible.

To aid an understanding of the single pressure source system 200, an exemplary embodiment in which the first flow circuit 204 and the second flow circuit 206 have different flow resistances, and hence, different volumetric flow rates of the first and second fluid, is illustrated below. Further, the first flow circuit 204 and the second flow circuit 206 can maintain constant, but different, first and second volumetric flow rates of the first fluid 102 and the second fluid 104, respectively. Hence, the differential between the first volumetric flow rate of the first fluid 102 and the second volumetric flow rate of the second fluid 104 also remains constant. In the exemplary embodiment, the first fluid 102 and the second fluid 104 are pressurized at five pounds per square inch (5 psi) by the pressure source 202. Further, the resistance (R1) of the first flow circuit 204 is such that for a pressure of 5 psi, a volumetric flow rate (Q1 proportional to P/R1) of 150 micro liters per minute (μl/min) is maintained for the first fluid 102. Similarly, the resistance (R2) of the second flow circuit 206 is such that for a pressure of 5 psi, a volumetric flow rate (Q2 proportional to P/R1) of five mille liters per minute (ml/min, i.e., 5000 μl/min) is maintained for the second fluid 104. Consequently, a differential volumetric flow rate ($\Delta Q$) of 4850 (5000–150 μl/min) can be maintained.

The change in the pressure of the pressure source 202, i.e., the pressure 'P', affects the volumetric flow rates of the first fluid 102 and the second fluid 104, since both the fluids are pressurized by the pressure source 202. If the pressure 'P' of the pressure source 202 increases by dP, the first volumetric flow rate (Q1) of the first fluid 102 changes from being proportional to P/R1 to being proportional to (P+dP)/R1 (Q1', as shown in equation 5). Similarly, the second volumetric flow rate (Q2) of the second fluid 104 changes from being proportional to P/R2, to being proportional to (P+dP)/R2 (Q2', as shown in equation 6). Further, the differential volumetric flow rate ($\Delta Q$) changes from being proportional to (P/R2−P/R1), to being proportional to (P+dP)/R2−(P+dP)/R1 ($\Delta Q'$, as shown in equation 7 and 8).

$$Q1' \propto \frac{P + dP}{R1} \quad \text{(Equation 5)}$$

$$Q2' \propto \frac{P + dP}{R2} \quad \text{(Equation 6)}$$

$$\Delta Q \propto \frac{P}{R2} - \frac{P}{R1} \quad \text{(Equation 7)}$$

$$\Delta Q' \propto \frac{P + dP}{R2} - \frac{P + dP}{R1} \quad \text{(Equation 8)}$$

Where dP is the change in the pressure of the pressure source, i.e., pressure 'P'.

R1 is the flow resistance of the first flow circuit 204.

R2 is the flow resistance of the second flow circuit 206.

The pressure 'P' of the pressure source 202 is controlled by a pressure regulator or a similar device. This pressure regulator can be used to regulate the pressure source for changing the first volumetric flow rate of the first fluid 102 and the second volumetric flow rate of the second fluid 104. Since the variations (dP) in the pressure 'P' are limited to the tolerance zone of only the pressure regulator, the variations in the differential volumetric flow rate is proportional to dP(1/R2−1/R1) (from equation 7 and equation 8). Whereas, if two regulators are used, as described in FIG. 1 (Prior Art), the change in the differential volumetric flow rate is more if one regulator operates at the positive extreme of the tolerance zone and the other operates at the negative extreme of the tolerance zone.

The first volumetric flow rate of the first fluid 102 and the second volumetric flow rate of the second fluid 104 can be altered by altering the resistances R1 and R2 of the first flow circuit 204 and second flow circuit 206, respectively. Further, the first and second volumetric flow rates can also be altered by altering the pressure 'P' of the pressure source 202. For example, to reduce the first volumetric flow rate (Q1) of the first fluid 102, the flow resistance of the first flow circuit 204 can be increased by introducing an additional flow restrictor or by replacing the existing flow restrictor by another flow restrictor with greater resistance. Consequently, the value of the differential volumetric flow rate ($\Delta Q$) can also be altered. To make the desired increase in the resistance (R1) of the first flow circuit 204, one or more flow restrictors may be introduced in the flow circuit 204. (This is described in conjunction with FIG. 4.). Further, the pressure 'P' can be adjusted in conjunction with or independent of the resistance of the flow circuits to change the absolute (Q1 and Q2) and the differential volumetric flow rate ($\Delta Q$) values. These values can be obtained experimentally or can be approximated with the aid of computational fluid dynamics.

Figure 3:
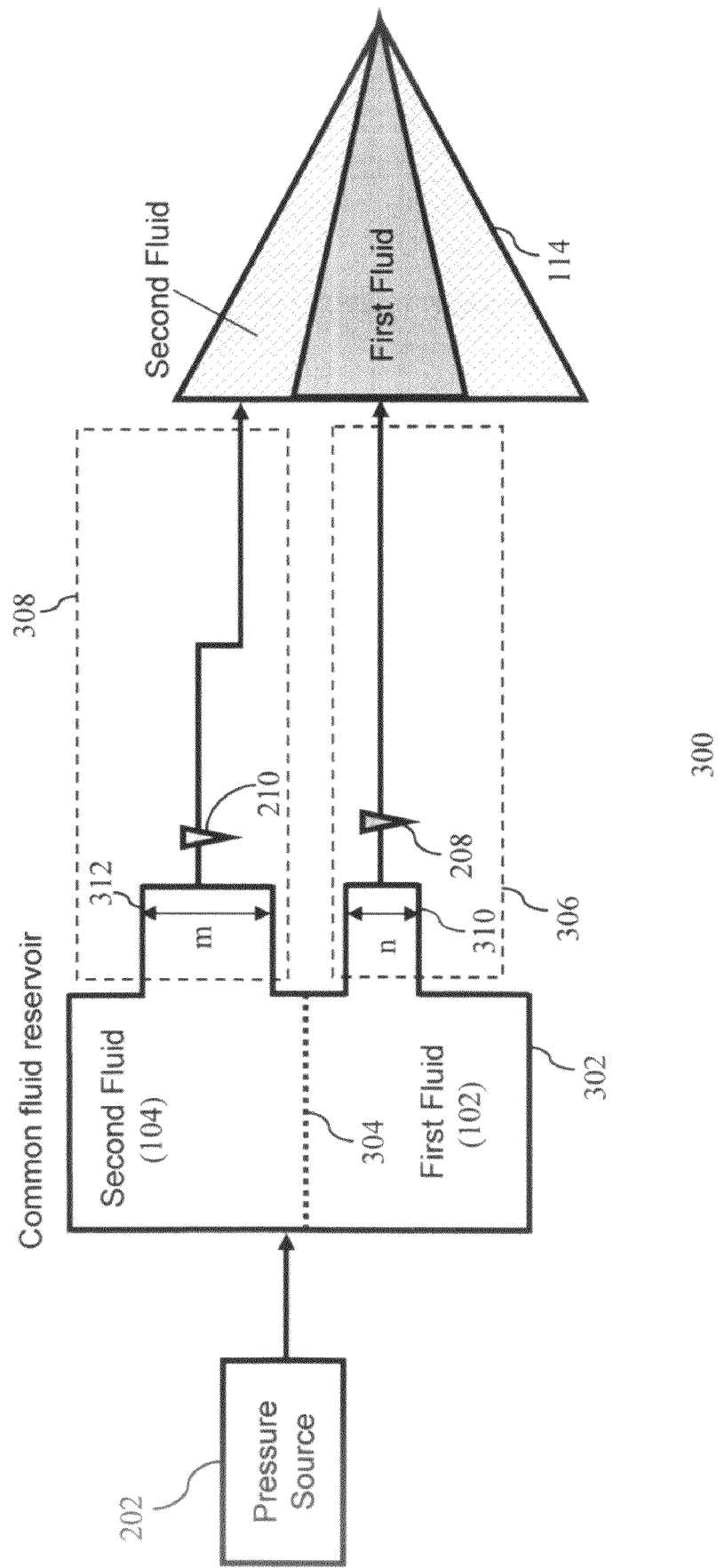
FIG. 3 illustrates a block diagram of a single pressure source system for obtaining the differential volumetric flow rate between two fluids, in accordance with another embodiment of the present invention.

FIG. 3 illustrates a block diagram of a single pressure source system 300 for obtaining a differential volumetric flow rate between two fluids, in accordance with another embodiment of the present invention. Those skilled in the art will appreciate that the single pressure source system 300 may include all or a fewer number of components than those shown in FIG. 3. Further, those of ordinary skill in the art will understand that the single pressure source system 300 may include additional components that are not shown here, since they are not germane to the operation of the single pressure source system 300, in accordance with the inventive arrangements.

In addition to the converging section 114, the pressure source 202, the first flow restrictor 208 and the second flow restrictor 210, the single pressure source system 300 is shown to include a common fluid reservoir 302, a partition member 304, a first flow circuit 306, and a second flow circuit 308. Further, the common fluid reservoir 302 is shown to include the integrated flow restrictors 310 and 312. The common fluid reservoir 302 has the first fluid 102 and the second fluid 104 on either side of the partition member 304. The pressure source 202 can pressurize the first fluid 102 and the second fluid 104 simultaneously. In one embodiment, the partition member 304 can be an impermeable but flexible membrane, or a selectively permeable membrane that is permeable to gases but not to liquids such as hydrophobic filters. In another embodiment, the partition member 304 can have a spool valve that can equalize the pressures of the first fluid 102 and the second fluid 104. A spool-valve arrangement can be a piston moving back and forth in a guide way that is open on both sides. The piston moves back and forth, depending on the pressure on either side of the guide way, equalizing pressure on both sides of the guide way. If the pressure source 202 pressurizes the first fluid 102 at a specified pressure, the second fluid 104 is also pressurized at the same pressure because of the spool valve arrangement. This avoids any difference between the pressure of the first fluid 102 and the second fluid 104. If the pressure on one of the fluid for example, the first fluid 102, increases, the partition member 304 with the spool-valve arrangement transmits the increased pressure to the second fluid 104 on the other side of the partition member 304. Consequently, the first fluid 102 and the second fluid 104 are pressurized at the same pressure.

In one embodiment, the pressure source 202 can be a gas pressure source. In this embodiment, the volumetric flow rate of the gas inducing the pressure on the fluid adjusts in accordance with the pressure 'P'. In other words, the flow rate of the gas pressurizing the fluid is dictated by the pressure value alone.

The integrated flow restrictor 310 is shown to be a hole, with a diameter of 'n' millimeters (mm), in the outlet duct for the first fluid 102 in the common fluid reservoir 302. Similarly, the integrated flow restrictor 312 is shown to be a hole, with a diameter of 'm' (mm), in the outlet duct for the second fluid 104 in the common fluid reservoir 302. The integrated flow restrictors 310 and 312 add to the overall resistance of the first flow circuit 306 and the second flow circuit 308, respectively.

Further, the presence of the integrated flow restrictors 310 and 312 enables the differential volumetric flow rate between the first fluid 102 and the second fluid 104 to be obtained without using the additional flow restrictors in the first fluid circuit 306 and the second fluid circuit 308, for example, the flow restrictors 208 and 210. For instance, if the resistance of the first flow circuit 306 is r1 when the first flow circuit 306 only has the integrated flow resistor 310, the first volumetric flow rate (Q1) of the first fluid 102 is proportional to P/r1. Similarly, if the resistance of the second flow circuit 308 is r2 when the second flow circuit 308 only has the integrated flow resistor 312, the second volumetric flow rate (Q2) of the second fluid 104 is proportional to P/r2. Consequently, the differential volumetric flow rate ($\Delta Q$), a value proportional to P/r2–P/r1 can be obtained when the first flow circuit 306 and the second flow circuit 308 have no additional flow restrictors, apart from the integrated flow restrictors 310 and 312 present in the common fluid reservoir 302.

By adding the additional flow restrictors 208 and 210 to the first flow circuit 306 and the second flow circuit 308, respectively, the overall resistance of the circuit can be changed. The resistance of the first flow circuit 306 and the second flow circuit 308 can change to r1' and r2' accordingly. Consequently, the differential volumetric flow rate ($\Delta Q$) is changed to be proportional to P/r2'–P/r1'.

The single pressure source system 300 can include various combinations of flow restrictors and flow orifices, in addition to the integrated flow restrictors 310 and 312, to obtain multiple values of the differential volumetric flow rate. However, for the purpose of this description, the single pressure source system 300 is shown to include the first flow restrictor 208 and the second flow restrictor 210. The first flow restrictor 208 and the second flow restrictor 210 function in a similar way, as described in conjunction with FIG. 2.

Figure 4:
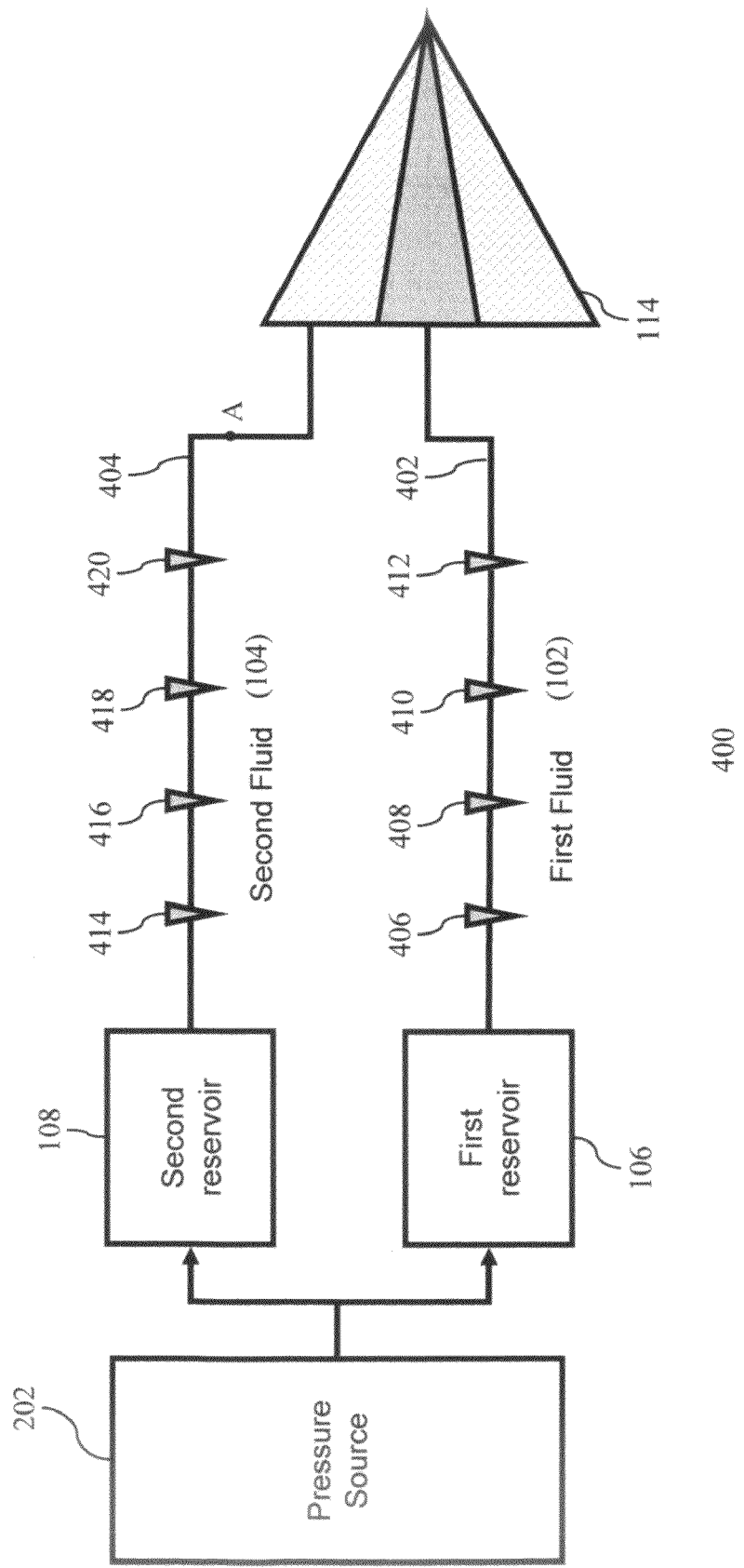
FIG. 4 illustrates a block diagram of a single pressure source system for obtaining the differential volumetric flow rate between two fluids, in accordance with another embodiment of the present invention.

FIG. 4 illustrates a block diagram of a single pressure source system 400 for obtaining the differential volumetric flow rate between two fluids, in accordance with another embodiment of the present invention. Those skilled in the art will appreciate that the single pressure source system 400 may include all or even a fewer number of components than the components shown in FIG. 4. Further, those with ordinary skill in the art will understand that the single pressure source system 400 may include additional components that are not shown here, since they are not germane to the operation of the single pressure source system 400, in accordance with the inventive arrangements.

The single pressure source system 400 can include flow circuits with various combinations of flow restrictors and flow orifices. For the purpose of this description, the single pressure source system 400 is shown to include a first flow circuit 402 through which the first fluid 102 flows and a second flow circuit 404 through which the second fluid 104 flows, in addition to the first reservoir 106, the second reservoir 108, the converging section 114, and the pressure source 202. Further, the first flow circuit 402 is shown to include the flow restrictors 406, 408, 410 and 412. Similarly, the second flow circuit 404 is shown to include the flow restrictors 414, 416, 418 and 420. The functioning of the pressure source 202, the first reservoir 106, the second reservoir 108 and the converging section 114 in the single pressure source system 400 is similar to their functioning described in FIGS. 1 and 2.

The pressure source 202 pressurizes the first fluid 102 stored in the first reservoir 106 and the second fluid 104 stored in the second reservoir 108 at the same pressure 'P'. Thereafter, the first fluid 102 flows through the first flow circuit 402 and the second fluid 104 flows through the second flow circuit 404.

The presence of first set of flow restrictors, for example, the flow restrictors 406, 408, 410, and 412, and the flow connectors in the first flow circuit 402, accounts for the overall resistance ($R1_{set}$) of the first flow circuit 402. Examples of flow connectors include, but are not limited to, tubes, conduits and the like. The flow connectors hydraulically connect the flow restrictors 406, 408, 410, and 412. The flow restrictors 406, 408, 410 and 412 are hydraulically connected in series passage flow circuit. The resistance of the first flow circuit 402 may be calculated by using appropriate formulae for each type of flow restrictor, for example, for a simple round tube, closed form formulae can be used. Similarly, for other types of restrictors, the resistance can be determined with the aid of computational fluid dynamics or other empirical means. Similarly, the second flow circuit 404 has second set of flow restrictors, for example, the flow restrictors 414, 416, 418, and 420, in the second flow circuit 404. Similar to the first set of flow restrictors 406, 408, 410 and 412, the second set of flow restrictors 414, 416, 418, and 420 are also hydraulically connected in a series passage flow circuit. The flow restrictors 414, 416, 418 and 420, and the flow connectors in the second flow circuit 404, accounts for the overall resistance ($R2_{set}$) of the second flow circuit 404. Consequently, the differential volumetric flow rate ($\Delta Q$) is proportional to $P/R2_{set} - P/R1_{set}$.

The flow resistances of the first flow circuit 402 and the second flow circuits 404 depends on the type and the number of flow restrictors in them. In one embodiment of the present invention, the first set of flow restrictors 406, 408, 410 and 412 can be designed to provide a first preset value of flow resistance. Similarly, the second set of flow restrictors 414, 416, 418, and 420 can be designed to provide a second preset value of flow resistance. The resistances of the flow circuits are preset to achieve a desired value of first and second flow rates and the differential volumetric flow rate.

In another embodiment of the present invention, at least one of the first set of flow restrictors 406, 408, 410 and 412 can be altered to adjust the flow resistance of the first flow circuit 402. Further, in this embodiment, at least one of the second set of flow restrictors 414, 416, 418, and 420 can be altered to adjust the flow resistance of the second flow circuit 404. The altering of the flow resistances can be performed to obtain different values of differential volumetric flow rate between the first fluid 102 and the second fluid 104.

Figure 5:
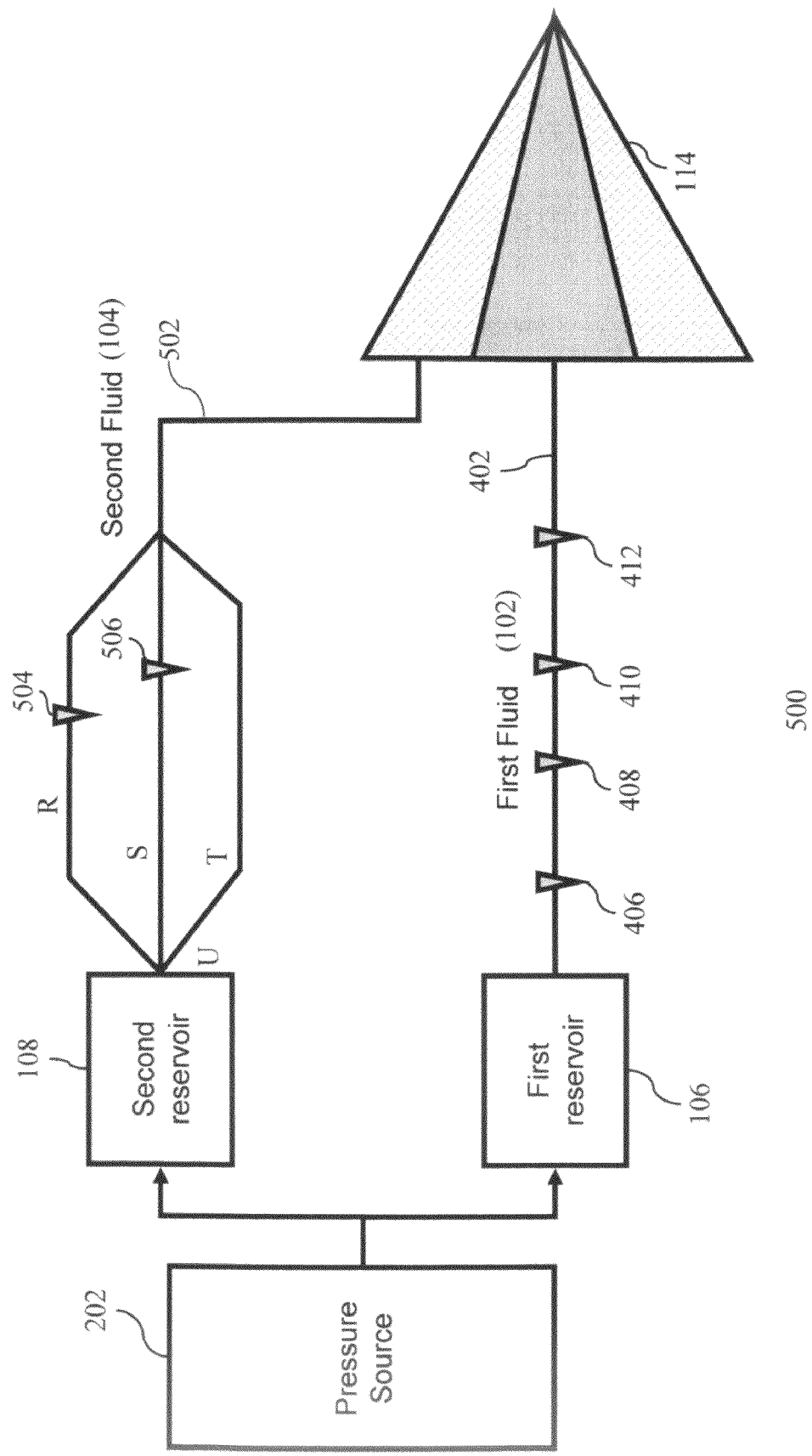
FIG. 5 illustrates a block diagram of a single pressure source system for obtaining the differential volumetric flow rate between two fluids, in accordance with yet another embodiment of the present invention.

FIG. 5 illustrates a block diagram of a single pressure source system 500 for obtaining the differential volumetric flow rate between two fluids, in accordance with still another embodiment of the present invention. Those skilled in the art will appreciate that the single pressure source system 500 may include all or even a fewer number of components than the components shown in FIG. 5. Further, those with ordinary skill in the art will understand that the single pressure source system 500 may include additional components that are not shown here, since they are not germane to the operation of the single pressure source system 500, in accordance with the inventive arrangements.

In addition to the converging section 114, the pressure source 202 and the first flow circuit 402, the single pressure source system 500 also includes a second flow circuit 502 through which the second fluid 104 is made to flow. The second flow circuit 502 is a parallel passage flow circuit, which can have multiple parallel flow passages. For the purpose of this description, the second flow circuit 502 is shown to include three different flow passages in parallel, for example, flow passage 'R', flow passage 'S' and flow passage 'T'. The flow of the second fluid 104 in the flow passages 'R', 'S' and 'T' can be controlled by a control switch (not shown in FIG. 5) at junction 'U'. The control switch can be operated to independently select one or more flow passages from the flow passages 'R', 'S' and 'T' through which the second fluid 104 can be made to flow. For example, the control switch can be operated to direct the second fluid 104 through any or all of the three flow passages. Further, the flow passages 'R', 'S' and 'T' can have various flow restrictors arranged in different combinations. For the purpose of this description, the flow passages 'R' and 'S' are shown to include the flow restrictors 504 and 506, respectively. The flow passage 'T' is shown not to have any flow restrictor for any additional resistance to flow through the flow passage 'T'. The resistance of the flow passages R and S, due to the presence of flow restrictors 504 and 506, are $R_R$ and $R_S$, respectively. Further, all the flow passages can be opened or closed, in various combinations, by the control switch at the junction 'U'. For example, the control switch at the junction 'U' can be operated to enable the second fluid 104 to flow through the flow passage 'R' resulting in a flow rate $Q2_R$. In another example, the control switch at the junction 'U' can be operated to enable the second fluid 104 to flow through the flow passage 'S' resulting in a flow rate $Q2_S$.

In another example, the control switch at the junction 'U' can be operated to enable a particular volume of the second fluid 104 to flow through the passage 'R' and the remaining volume to flow through the passage 'S'. In this example, the overall resistance of the second flow circuit 502 can be calculated by using appropriate formulae for each type of flow restrictor and the combinations of flow passages used to control the flow of the second fluid 104. The resistance can also be determined with the aid of computational fluid dynamics or other empirical means. Consequently, different values of the second volumetric flow rate (Q2) can be obtained.

Different values of the differential volumetric flow rate can also be obtained by varying the pressure 'P' and/or the resistances of either or both the first flow circuit 402 and the second flow circuit 502. Further, the single pressure source system 500 can include various combinations of flow restrictors and flow orifices, to obtain the multiple values of the differential volumetric flow rate.

Figure 6:
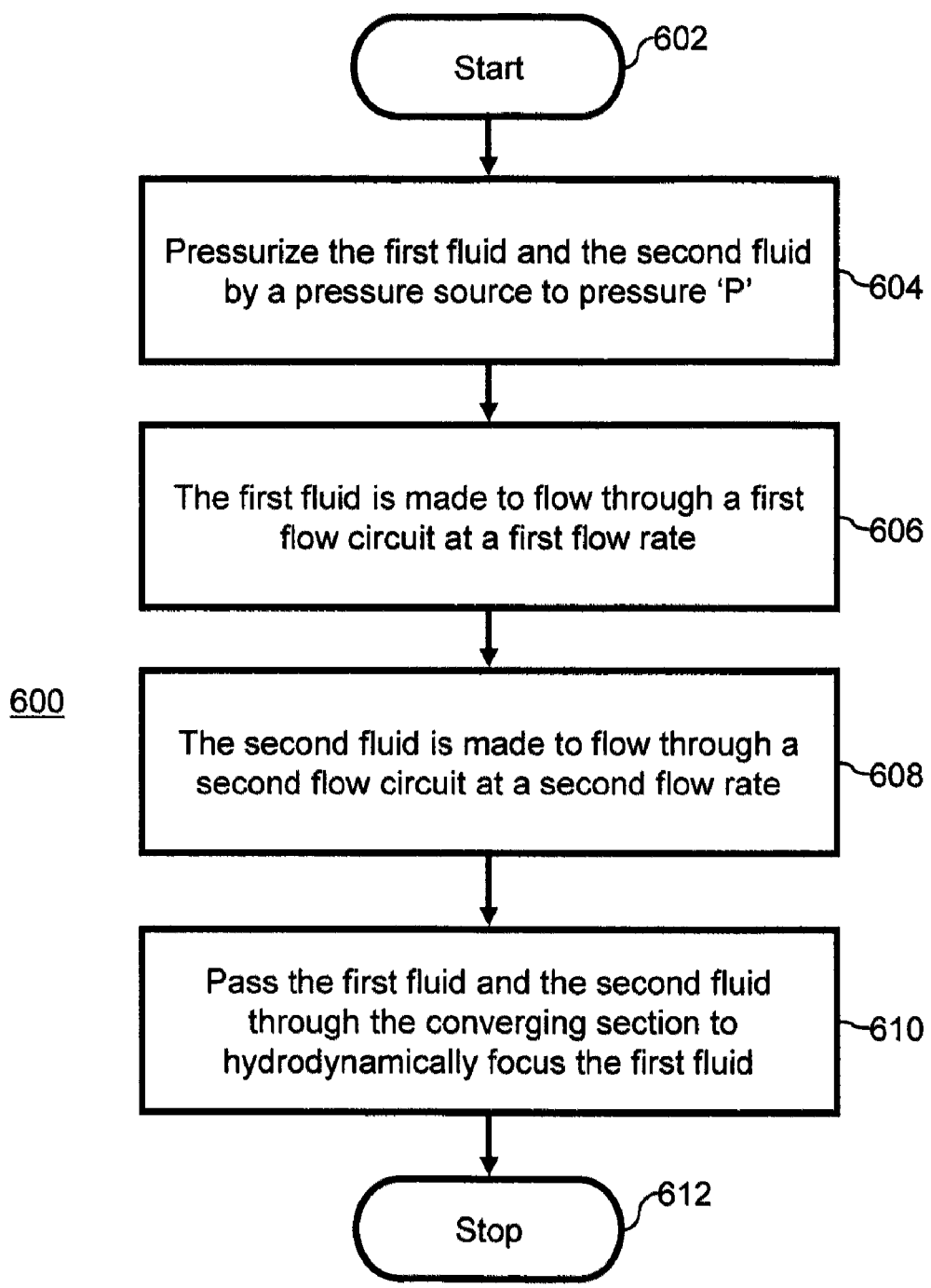
FIG. 6 is a flowchart illustrating a method for hydrodynamic focusing of a first fluid in a flow cytometer, in accordance with an embodiment of the present invention.

FIG. 6 is a flowchart illustrating a method hydrodynamic focusing of a first fluid in a flow cytometer, in accordance with an embodiment of the present invention. To describe the flowchart 600, reference is made to FIGS. 1, 2, 3, 4 and 5, although it should be understood that the flowchart 600 can also be implemented in any other suitable environment or network. Moreover, the invention is not limited to the order in which the steps are listed in the flowchart 600.

The method for hydrodynamic focusing of a first fluid in a flow cytometer is initiated at step 602. At step 604, the first fluid 102 and the second fluid 104 are pressurized to pressure 'P' by using the pressure source 202. Examples of the pressure source 202 can include a positive volume-displacement device such as a syringe pump or any other pressure source that can apply constant pressure on the first fluid 102 and the second fluid 104. Since the same pressure source 202 is used to pressurize the first fluid 102 and the second fluid 104, the pressure applied on both the fluids is the same, i.e., pressure 'P'.

At step 606, the first fluid 102 is made to flow through a first flow circuit. The first fluid is made to flow through a first flow rate, or a first volumetric flow rate. Examples of the first flow circuit may include, but are not limited to, the first flow circuit 204, the first flow circuit 306, the first flow circuit 402 or other flow circuits designed to obtain the first flow rate of the first fluid 102. In an embodiment, the first flow circuit can be a pipe, tubing or passage through which the first fluid 102 is made to flow. The first flow circuit can have variable bends, restrictors or flow orifices to control the volumetric flow rate of the first fluid 102. At step 608, the second fluid 104 is made to flow through a second flow circuit. The second fluid is made to flow at a second flow rate, or a second volumetric flow rate. Examples of the second flow circuit may include, but are not limited to, the second flow circuit 206, the second flow circuit 308, the second flow circuit 404, the second flow circuit 502 or any other flow circuit designed obtain the second flow rate of the second fluid 104. The flow restrictors in the first fluid circuit and the second fluid circuit can be adjusted to change the first flow and the second flow. Consequently, the differential volumetric flow rate is changed. In one embodiment of the invention, the pressure 'P' at which the pressure source 202 pressurizes the first fluid 102 and the second fluid 104 can be changed to change the differential volumetric flow rate. The pressure 'P' can be changed by using a regulator of the pressure source 202. At step 610, the first fluid 102 and the second fluid 104 are made to pass through the converging section 114 to hydrodynamically focus the first fluid 102. The differential volumetric flow rates between the first fluid 102 and the second fluid 104 causes hydrodynamic focusing of the first fluid 102.

Figure 7:
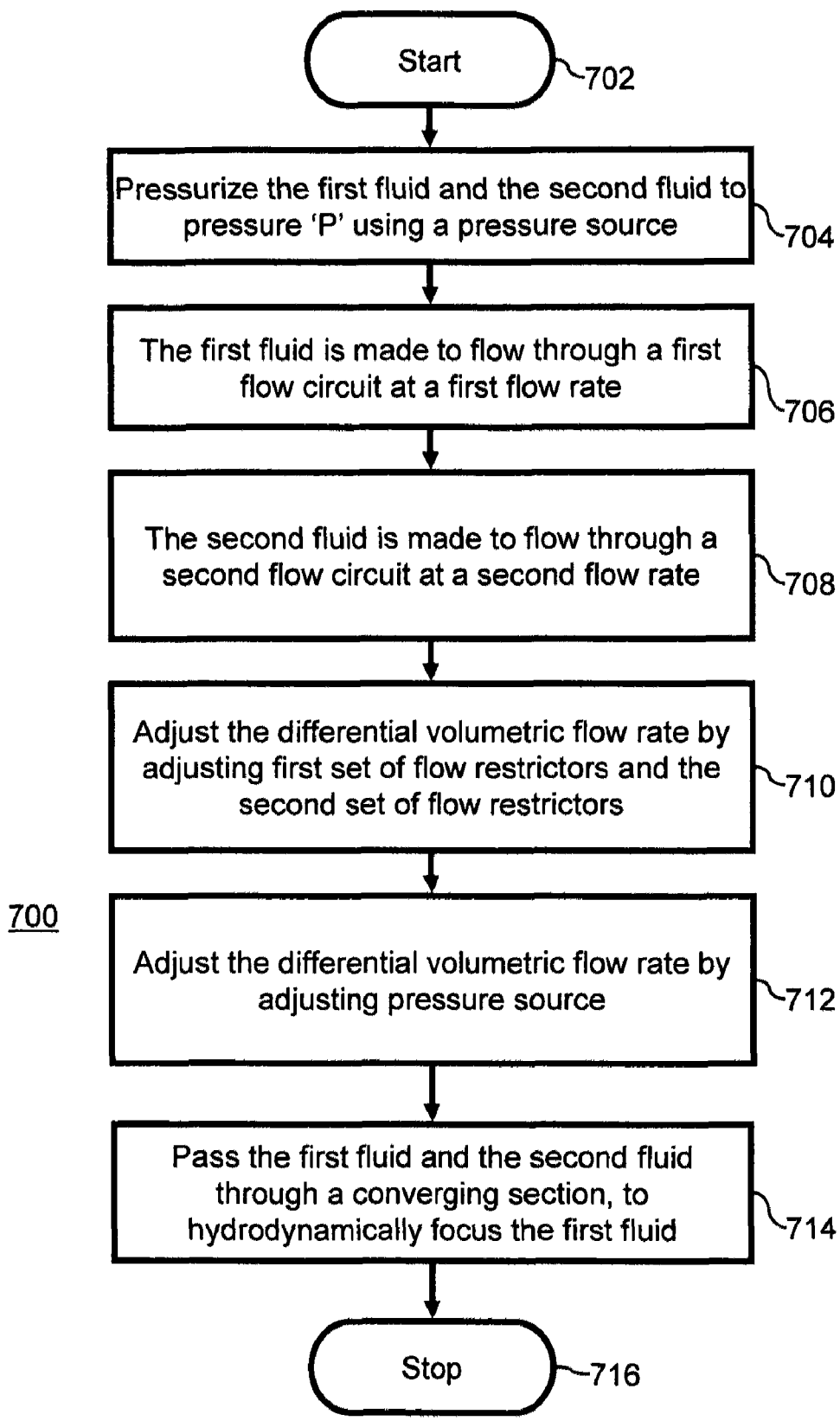
FIG. 7 is a flowchart illustrating a method for hydrodynamic focusing of the first fluid in a flow cytometer, in accordance with another embodiment of the present invention.

FIG. 7 is a flowchart illustrating a method for hydrodynamic focusing of the first fluid 102 in a flow cytometer, in accordance with an embodiment of the present invention. To describe the flowchart 600, reference is made to FIGS. 1, 2, 3, 4 and 5, although it should be understood that the flowchart 700 can also be implemented in any other suitable environment or network. Moreover, the invention is not limited to the order in which the steps are listed in the flowchart 700.

The method for hydrodynamically focusing the first fluid 102 is initiated at step 702. At step 704, the first fluid 102 and the second fluid 104 are pressurized to pressure 'P' by using the pressure source 202. Examples of the pressure source 202 can include a positive volume-displacement device such as a syringe pump or any other pressure source that can apply constant pressure on the first fluid 102 and the second fluid 104. Since the same pressure source is used to pressurize the first fluid 102 and the second fluid 104, the pressure applied on both the fluids is the same, i.e., the pressure 'P'.

At step 706, the first fluid 102 is made to flow through a first flow circuit at a first flow rate. Examples of the first flow circuit may include, but are not limited to, the first flow circuit 204, the first flow circuit 306, the first flow circuit 402 or other flow circuits designed to obtain the first flow rate of the first fluid 102. In an embodiment, the first flow circuit can be a pipe, tubing or passage through which the first fluid 102 is made to flow. The first flow circuit can have variable bends, restrictors or flow orifices to control the volumetric flow rate of the first fluid 102. At step 708, the second fluid 104 is made to flow through a second flow circuit at a second flow rate. Examples of the second flow circuit may include, but are not limited to, the second flow circuit 206, the second flow circuit 308, the second flow circuit 404, the second flow circuit 502 or any other flow circuit designed to control the second flow rate of the second fluid 104.

At step 710, the differential volumetric flow rate is adjusted by adjusting the resistance of the first set of flow restrictors of the first flow circuit and the resistance of the second set of flow restrictors of the second flow circuit. The resistance of the first set of flow restrictors and the second set of flow restrictors can be adjusted manually or electronically by adjusting and/or adding the flow restrictors of the flow circuits. Different combinations of these flow restrictors can be used to control the resistance of the two circuits, and consequently, the respective flow rates. The flow restrictors are used to obtain the specific value of the volumetric flow rates and can be adjusted to obtain variable or fixed volumetric flow rates of the fluid flowing through them, in conjunction with or independent of the changing pressure. Examples of flow restrictors include, but are not limited to, a calibrated orifice, pinch valves, and plate or flange restrictors. Further, the resistances of the first and second flow circuits can also be changed by changing various parameters of the flow connectors, for example, the length, the cross-sectional area, the fluidic connection, the number of bends, and the like. The difference between the first flow rate and the second flow rate generates a differential flow rate between the first fluid 102 and the second fluid 104.

The first flow circuit and the second flow circuit can also be arranged in various combinations or sequences. The multiple values of the differential volumetric flow rate between the first fluid 102 and the second fluid 104 can be obtained by incorporating multiple independent flow circuits and switching between them. For example, the second fluid 104 can be passed through a flow circuit with three different flow passages with different flow resistance (as described in FIG. 5).

At step 712, the differential volumetric flow rate is adjusted by adjusting the pressure source 202. As the pressure source 202 pressurizes both the first fluid 102 and the second fluid 104, the flow rates of both the fluid can be adjusted by adjusting the pressure source 202. The pressure source 202 can be adjusted by a pressure regulator of the pressure source 202. At step 714, the first fluid 102 and the second fluid 104 are passed through the converging section 114 to hydrodynamically focus the first fluid 102 in the second fluid 104. The first fluid 104 is hydrodynamically focused because of the differential volumetric flow rate between the first fluid 102 and the second fluid 104.

FIG. 8 illustrates exemplary laboratory equipment 800, in accordance with an embodiment of the present invention. In a preferred embodiment, the laboratory equipment is a flow cytometer. Those skilled in the art will appreciate that the laboratory equipment 800 may include all or a fewer number of components than those shown in FIG. 8. Further, those with ordinary skill in the art will understand that the laboratory equipment 800 may include additional components that are not shown here, since they are not germane to the operation of the laboratory equipment 800, in accordance with the inventive arrangements.

The laboratory equipment 800 is shown to include a first flow circuit 802 and a second flow circuit 804, in addition to the first fluid 102, the second fluid 104, the first reservoir 106, the second reservoir 108, the converging section 114 and the pressure source 202. Examples of the laboratory equipment include, but are not limited to, a cuvette, a funnel, a pipette, or a tube with a converging region at one end. The first fluid 102, which is stored in the first reservoir 106, is pressurized by the pressure source 202 into the first flow circuit 802. Similarly, the second fluid 104, which is stored in the second reservoir 108, is pressurized by the pressure source 202 into the second flow circuit 804. The first reservoir 106 and the second reservoir 108 provide the first fluid 102 and the second fluid 104 to the first flow circuit 802 and the second flow circuit 804, respectively. Examples of the first flow circuit 802 may include, but are not limited to, the first flow circuit 202, the first flow circuit 402, and any other flow circuit to control the volumetric flow rate of the first fluid 102. Examples of the second flow circuit 804 include, but are not limited to, the second flow circuit 206, the second flow circuit 404, the second flow circuit 502, and any other flow circuit to control the volumetric flow rate of the second fluid 104. The first flow circuit 802 and the second flow circuit 804 are designed to maintain the specified values of the volumetric flow rates of the fluids flowing through them. For example, the first flow circuit 802 can maintain a volumetric flow rate of 150 µl/min, and the second flow circuit 804 can maintain a volumetric flow rate of 5 ml/min. The first fluid 102 is fed into the laboratory equipment 800 with the second fluid 104. The second fluid 104 flows such that the second fluid 104 annularly envelopes the first fluid 102. Further, the first fluid 102 is hydrodynamically focused in the second fluid 104.

The converging section 114 at one end of the laboratory equipment 800 is a geometrically structured cavity that can converge the flow stream diameters of the first fluid 102 and the second fluid 104. The first fluid 102 flowing at the core of the laboratory equipment 800 is shrunk in the stream diameter. The second fluid 104 forms an annular envelope around the first fluid 102. Furthermore, the first fluid 102 is focused by the hydrodynamic forces generated due to the differential volumetric flow rate between the first fluid 102 and the second fluid 104. Moreover, there is no physical boundary between the first fluid 102 and the second fluid 104 in the converging section 114.

Further, the constant differential volumetric flow rate between the first fluid 102 and the second fluid 104 can be used to generate a thin stream of the first fluid 102. In other words, the hydrodynamic focusing of the first fluid 102 is performed. The thin stream of the first fluid 102 can be analyzed to count microscopic particles by examining its physical and chemical properties. The microscopic particles can be analyzed by using an optical or electronic method of analysis. To obtain the optimum shrinkage of the first fluid 102, a constant check is maintained on the differential pressure or volumetric flow rate of the first fluid 102 and the second fluid 104.

Various embodiments of the present invention offer one or more advantages. The present invention provides a system and method for generating a differential volumetric flow rate. There is only one source of pressure, therefore a change in the pressure of the first fluid will automatically be reflected in the second fluid, and the resultant change in the differential volumetric flow rate is minimized. Further, there are no independent changes in the pressures of the first and the second fluid, therefore tracking the changes in differential pressure is not required. Consequently, the present system and method eliminates the need for a feedback system. The new system, without the feedback system, is simple and cost-effective. The new system does not make use of two pressure regulators, hence minimizing any error due to tolerances in the mechanical and electrical parts of the pressure regulators. Furthermore, a constant difference in the volumetric flow rate is maintained and controlled through different flow restrictors. Consequently, a variation in stream diameter of the first fluid is minimized. Moreover, the elimination of a second pressure source also reduces the cost.

What is claimed is:

1. A method for hydrodynamic focusing of a first fluid within a second fluid in a flow cytometer, the method comprising the steps of:
pressurizing the first fluid and the second fluid at a pre-defined pressure, the first fluid and the second fluid being pressurized using a pressure source;
controlling a first flow rate corresponding to the first fluid, the first flow rate being controlled by flow resistance of a first flow circuit downstream of the pressure source;
controlling a second flow rate corresponding to the second fluid, wherein the second flow rate is controlled by flow resistance of a second flow circuit downstream of the pressure source; and
passing the first fluid and the second fluid through a converging section, wherein
the first fluid is hydrodynamically focused in the converging section; and
altering at least one of the first and second flow rates by reconfiguring the corresponding flow resistance of at least one of the first and second flow circuits;
wherein the pre-defined pressure is non-independently applied against both the first and second fluids upstream from the first and second flow circuits while altering at least one of the first and second flow rates.

2. The method according to claim 1, wherein the first flow circuit comprises a first set of flow restrictors, the first set of flow restrictors corresponding to a first set of flow resistances.

3. The method according to claim 2, wherein the first set of flow restrictors are connected in at least one of a parallel passage flow circuit and a series passage flow circuit.

4. The method according to claim 2 further comprising the step of altering at least one of the first set of flow resistances to adjust the first flow rate.

5. The method according to claim 1, wherein the second flow circuit comprises a second set of flow restrictors, the second set of flow restrictors corresponding to a second set of flow resistances.

6. The method according to claim 5, wherein the second set of flow restrictors are connected in at least one of a parallel passage flow circuit and a series passage flow circuit.

7. The method according to claim 5 further comprising the step of altering the second set of flow resistances to adjust the second flow rate.

8. The method according to claim 1 further comprising the step of altering the pre-defined pressure to adjust at least one of the first flow rate and the second flow rate.

9. The method according to claim 5, wherein at least one of the first set of flow restrictors and the second set of flow restrictors are connected in at least one of a parallel passage flow circuit and a series passage flow circuit.

10. The method according to claim 1, wherein pressure is non-independently regulated against both the first and second fluids upstream from the first and second flow circuits while altering at least one of the first and second flow rates.

11. The method according to claim 1, wherein the second flow circuit comprises a plurality of flow passages that can each be opened and closed.

12. The method according to claim 11, wherein the first flow circuit comprises a single flow passage.

* * * * *